United States Patent
Rustemeyer et al.

(10) Patent No.: US 9,010,338 B2
(45) Date of Patent: Apr. 21, 2015

(54) BIODEGRADABLE PLASTIC AND USE THEREOF

(75) Inventors: Paul Rustemeyer, Gundelfingen (DE); Wolfgang Koppe, Merzhausen (DE); Dirk Hölter, Emmendingen (DE)

(73) Assignee: Solvay Acetow GmbH, Freiburg (DE)

( * ) Notice: Subject to any disclaimer, the term of this patent is extended or adjusted under 35 U.S.C. 154(b) by 108 days.

(21) Appl. No.: 13/124,226

(22) PCT Filed: Sep. 17, 2009

(86) PCT No.: PCT/EP2009/006734
§ 371 (c)(1),
(2), (4) Date: Apr. 14, 2011

(87) PCT Pub. No.: WO2010/043293
PCT Pub. Date: Apr. 22, 2010

(65) Prior Publication Data
US 2011/0197642 A1    Aug. 18, 2011

(30) Foreign Application Priority Data
Oct. 14, 2008 (DE) .......................... 10 2008 051 579

(51) Int. Cl.
| | |
|---|---|
| A24D 3/00 | (2006.01) |
| C08L 101/16 | (2006.01) |
| A01N 25/10 | (2006.01) |
| C05G 3/00 | (2006.01) |
| C08J 5/18 | (2006.01) |
| C08K 3/22 | (2006.01) |
| C08K 5/00 | (2006.01) |
| C08K 5/1545 | (2006.01) |
| C08L 1/12 | (2006.01) |
| C08L 1/14 | (2006.01) |
| D01F 1/10 | (2006.01) |
| D01F 2/28 | (2006.01) |

(52) U.S. Cl.
CPC ......... *C08L 101/16* (2013.01); *C08K 2201/005* (2013.01); *A01N 25/10* (2013.01); *C05G 3/0047* (2013.01); *C08J 5/18* (2013.01); *C08J 2301/12* (2013.01); *C08K 3/22* (2013.01); *C08K 5/0033* (2013.01); *C08K 5/1545* (2013.01); *C08L 1/12* (2013.01); *C08L 1/14* (2013.01); *C08L 2201/06* (2013.01); *D01F 1/10* (2013.01); *D01F 2/28* (2013.01)

(58) Field of Classification Search
CPC ............... C08K 5/0033; C08K 3/0033; C08K 2201/005; C08L 1/12; C08L 2201/06
USPC ................. 524/31; 106/170.15; 131/342, 345
See application file for complete search history.

(56) References Cited

U.S. PATENT DOCUMENTS

| | | | |
|---|---|---|---|
| 5,478,386 A | 12/1995 | Itoh et al. | |
| 5,720,803 A | 2/1998 | Itoh et al. | |
| 6,571,802 B1 * | 6/2003 | Yamashita | 131/332 |
| 6,739,344 B2 * | 5/2004 | Yamashita | 131/345 |
| 2002/0123546 A1 | 9/2002 | Bigg et al. | |
| 2008/0087290 A1 * | 4/2008 | Taniguchi et al. | 131/332 |
| 2009/0151738 A1 * | 6/2009 | Robertson et al. | 131/332 |

FOREIGN PATENT DOCUMENTS

| | | |
|---|---|---|
| CN | 1088595 A | 6/1994 |
| CN | 1309145 A | 8/2001 |
| CN | 1343267 A | 4/2002 |
| CN | 1352665 A | 6/2002 |
| CN | 1683446 A | 10/2005 |
| EP | 0 632 968 A2 | 5/1994 |
| EP | 0 632 969 A2 | 5/1994 |
| EP | 0 394 803 | 12/1994 |
| EP | 0 777 977 A2 | 6/1997 |
| EP | 1 221 869 B1 | 1/2004 |
| JP | H7031452 * | 2/1995 |
| JP | 2004027079 | 1/2004 |
| WO | WO 92/20738 | 11/1992 |
| WO | WO 93/97771 | 4/1993 |
| WO | WO 94/10238 | 5/1994 |
| WO | WO 00/12616 | 3/2000 |

OTHER PUBLICATIONS

English-language Translation of JPH7-031452A, performed on the JPO website on Feb. 4, 2013 at 22:49:19 JST.*
Rinaudo, M., "Polysaccharides," Kirk-Othmer Encyclopedia of Chemical Technology. vol. 20, 1-42. Published online 2005.*
Ash, M., et al., "Calcium phosphate dibasic," Handbook of Food Additives, Third Edition, p. 989, 2008.*
Patent Office of the Russian Federation, Federal Institute of Industrial Property, Office Action (Inquiry) of the State Examination, 14.0-1. 2013.
State Intellectual Property Office of the People's Republic of China, Notification of the Second Office Action, Mar. 27, 2013.

* cited by examiner

*Primary Examiner* — Liam J Heincer
*Assistant Examiner* — Nicholas Hill

(57) ABSTRACT

The invention relates to a biodegradable plastic having increased biodegradation speed. Said plastic comprises a) finely distributed particle of a biodegradable, water-soluble, organic component, and b) finely distributed particles of a water-soluble, inorganic component promoting the growth of microorganisms and comprising N, P, and/or S. Said plastic is particularly based on cellulose esters such as cellulose acetate. Preferable components A are water-soluble saccharides and/or water-soluble organic acids. Said particularly advantageous biodegradable plastic is particularly available in the form of fibers, films, injection molded items, granulate beads, and containers. Controlled-release biocides and/or fertilizers can also be included in the molded part, wherein the molded part is degraded faster in the environment as said ingredients are released. The accelerated biodegradation is based on a synergistic interaction of the components indicated.

12 Claims, No Drawings

BIODEGRADABLE PLASTIC AND USE THEREOF

The invention relates to a biodegradable plastic with an increased biodegradation speed and advantageous uses thereof.

The biodegradation of plastics is desirable in many areas, thus, for example, in conjunction with the compostability of plastic bags for compostable fuels, for plastic items, which are carelessly thrown into the environment, such as, for example, cigarette ends, which should be rapidly biodegraded, for items which are to decompose in earth because of their intended use, such as, for example, flower pots, which can be buried together with the plant, or for "slow-release systems" in the agricultural sector, in which due to the biological decay of a polymer matrix, the active ingredients or biocides incorporated therein are gradually released.

U.S. Pat. No. 5,478,386 proposes acceleration in the degradation of discarded cigarette ends, in which the filter material is based on cellulose acetate, in that at least approximately 10% by weight of a cellulose acetate of a substitution degree of less than 2.5 is used. This is to achieve a 4 week degradation rate of at least 60% by weight in accordance with the determination method TM125209-91. For the degradation of filter tow, consisting of cellulose acetate, filaments, or and/or cellulose acetate staple fibres, EP 0 632 969 B1 makes the proposal of hydrolysing, in an alkaline manner, cellulose acetate located on the surface of the filaments or staple fibres in order to adjust the acetyl value to less than 53% and to thus promote the biodegradation. The teaching of EP 0 632 968 B1 intends to accelerate the degradation in that additives of enzymes splitting off cellulose chains are included in order to reduce the acetyl value to less than 53%. EP 0 777 977 A2 deals with degradable cigarettes, a readily degradable polymer mix being used. EP 1 221 869 B1 proposes including N-containing compounds which are distributed in a molecularly dispersed manner in the degradable plastic. PCT/AT92/00126 makes a further proposal to improve the degradability of plastics, according to which water-soluble or water-insoluble compounds are added, which are more rapidly degradable. The effect of this proposal in this regard was tested. Thus, cellulose diacetate fibres were produced, in which sugar or sodium chloride were in each case ground into particles smaller than 2 μm and spun in in a fraction of 5 to 10% by weight. No significantly accelerated degradation was ascertained beyond the pure release of the water-soluble components in the earth buying test mentioned below in more detail.

The invention was therefore based on the object of providing a technical proposal according to which biodegradable plastics have an increased biodegradation speed.

According to the invention, this object is achieved by a biodegradable plastic, characterised in that the plastic a) contains finely distributed particles of a biodegradable, water-soluble, organic component and b) finely distributed particles of a water-soluble, inorganic component containing N, P and/or S and promoting the growth of microorganisms.

It was surprisingly found that an accelerated biodegradation takes place in a biodegradable plastic when the latter contains a) finely distributed particles of a biodegradable, water-soluble, organic component, such as, for example, a sugar and, moreover, b) finely distributed particles of a water-soluble inorganic component containing N, P and/or S and promoting the growth of organic microorganisms when the latter were spun, for example, into cellulose acetate threads, which were later processed into a filter tow. Proceeding from this realisation, the teaching according to the invention was further developed. Preferred configurations of this will be shown below:

The invention is not subject to any substantial restrictions in the selection of the biodegradable plastic. It is preferred that the biodegradable plastic be based on cellulose ester, in particular cellulose acetate, cellulose acetate propionate and/or cellulose acetate butyrate, polylactide, polycaprolactone and/or polyhydroxybutyric acid, poly(lactide-co-glycolide), polylactide-polyglycol block copolymers. The use of mixtures may therefore also be advantageous.

There are also no relevant material-qualitative restrictions for component a). Water-soluble saccharides and/or water-soluble organic acids are preferred. Of the water-soluble saccharides, saccharose, glucose, maltose and/or lactose are preferred. Oxalic acid, malonic acid, glutaric acid, adipic acid, hydroxycarboxylic acids, in particular lactic acid, malic acid, tartaric acid, citric acid and/or ascorbic acid and/or amino carboxylic acids are considered to be the preferred water-soluble organic acids. These may thus be used in pure form or in a mixture.

The preferred component a) also includes water-soluble inorganic nitrogen compounds and/or water-soluble organic phosphorus compounds. Urea, guanidine, hexamethylenetetramine, glycine and/or alanine are also considered preferred water-soluble organic nitrogen compounds here.

The following should be stated with regard to the preferred qualitative assessment of component b): it is preferred for the component b) to be present in the form of salts containing Cl, K, Mg, Ca and/or Fe, the salts being quite particularly preferred in the form of $Na(NH_4)_2PO_4$, $NaH_2PO_4$, $Na_2SO_4$, $(NH_4)_2SO_4$, $NH_4NO_3$, $NaNO_3$, $MgSO_4$, $KH_2PO_4$, $FeSO_4$ and/or $NH_4Cl$. Particular possibilities are water-soluble salts of phosphoric acid, such as ammonium orthophosphate $((NH_4)_3PO_4.3H_2O)$, diammonium hydrogen orthophosphate $((NH_4)_2HPO_4.3H_2O)$, ammonium dihydrogen orthophosphate $((NH_4)H_2PO_4.3H_2O)$, sodium orthophosphate $(Na_3PO_4.12H_2O)$, sodium orthophosphate $(Na_3PO_4.10H_2O)$, disodium hydrogen phosphate $(Na_2HPO_4.2H_2O)$, disodium hydrogen phosphate $(Na_2HPO_4.12H_2O)$, sodium hydrogen phosphate $(NaH_2PO_4.2H_2O)$, sodium pyrophosphate $(Na_2H_2P_2O_7.6H_2O)$, sodium ammonium hydrogen phosphate $(NaH(NH_4)PO_4.4H_2O)$, potassium tetrametaphoshate $((KPO_3)_4.2H_2O)$, potassium orthophosphate $(K_3PO_4)$, potassium dihydrogen phosphate $(KH_2PO_4)$, potassium monohydrogen phosphate $(K_2HPO_4)$, potassium pyrophosphate $(K_4P_2O_7.3H_2O)$ and potassium subphosphate $(K_2PO_3.4H_2O)$. These substances b) may be present in pure form or a mixture and this, in particular, in crystalline form.

The effect aimed for according to the invention of increased biodegradability is not only advantageously determined by the qualitative variables given above. Rather, it is expedient that the component a) has a mean particle size of less than approximately 10 μm, in particular less than approximately 5 μm. A mean particle size of less than 2 μm is particularly preferred here, a particle size of less than 1 μm being quite particularly preferred. The preferred particle size of component b) is less than 10 μm, in particular less than 5 μm. Still better results are achieved if the component b) has a mean particle size of less than approximately 2 μm, in particular less than approximately 1 μm.

In order to achieve the object posed particularly favourably in the scope of the teaching according to the invention, it is advantageous to observe preferred quantitative framework conditions: thus, it is expedient for the component a) in the biodegradable plastic to be contained in a quantity of approximately 0.1 to 40% by weight, in particular approximately 1 to 20% by weight, the range of approximately 5 to 10% by weight being particularly preferred. The component b) is preferably contained in the biodegradable plastic in a quantity of approximately 0.01 to 20% by weight, in particular approximately 0.2 to 10% by weight. The particularly preferred range is to be disclosed here at approximately 0.3 to 3% by weight.

The teaching according to the invention designated above is described in a general account with respect to a biodegradable plastic with increased biodegradability. In practice, this biodegradable plastic is, in particular, present as a moulded part. These may, in particular, be fibres, films, such as deep-drawn films, in particular for use as packaging materials, injection-moulded articles, thick-walled moulded parts, granulates, microbeads, beads and vessels, in particular flower pots.

A particularly interesting application is that the moulded part, for example present as a granulate, microbeads, beads, contains releasable biocides or active agricultural agents and/or fertilisers. The active agricultural agents or biocides include, for example, fungicides, pesticides, herbicides, bactericides and/or insecticides. Nutrient fertilisers, such as nitrogen, phosphate, potassium, lime and magnesium fertilisers, mineral multi-nutrient fertilisers, such as NPK fertilisers, NP fertilisers, NK fertilisers and PA fertilisers, which were previously also referred to as mixed fertilisers, may be disclosed as fertilisers. Mixed fertilisers containing nitrogen, phosphate and potassium are particularly possible and are called complete fertilisers. The nitrogen fertilisers include, for example, ammonium sulphate, ammonium nitrate lime, urea, urea-aldehyde condensates, nitrogen magnesia, ammonium sulphate nitrate, nitrocalcite and calcium cyanamide. Possible pure phosphate fertilisers according to the invention are, for example, superphosphate, doublesuperphosphate and triplesuperphoshate, Thomas ground basic slag and/or Thomas phosphate, dicalcium phosphate. The particularly suitable calcium phosphates include apatite and phosphorite. The advantageous potassium fertilisers include potassium chloride and potassium sulphate and potassium salts containing magnesium such as potassium magnesia. Calcium and magnesium fertilisers which can be used are, for example, calcium carbonate, calcium oxide. The above list is not exhaustive.

The practical realisation of the present invention in the form of moulded parts increasingly also addresses the use of the biodegradable plastic according to the invention. Thus, it is particularly advantageous if, with the plastic according to the invention, threads are used, in particular for further processing into filter tow. In this case, this filter tow is preferably based on cellulose acetate, cellulose acetate butyrate or cellulose acetate propionate. In this case, these threads provided for further processing into filter tow are produced by generally known dry spinning methods However, the invention also proves to be particularly advantageous if films are produced using the biodegradable plastic according to the invention. In this case, in particular, a solution is further processed into films by the film casting method or a melt of the plastic is further processed into films by the flat extrusion or the film blowing method.

The invention can be technologically explained as follows without being regarded as binding: surprisingly, the inventors have found that a greatly accelerated degradation of the biodegradable plastic takes place when, apart from sugar, as the water-soluble component, to a small extent, salts with ammonium, phosphate or sulphate groups are spun into cellulose acetate threads, this being in the form of finely distributed particles. A generalisation could be made from this with further tests. It was established that this effect could also be shown when spinning in a larger quantity of salt-containing cellulose diacetate threads. The inventors carried out further tests for this purpose and these are recorded in the following Table I. The values of Table I were determined with the aid of the DIN specification EN ISO 11721-1. This is firstly directed at determining the resistance of cellulose-containing textiles against microorganisms according to the "earth burying test". The biodegradation-promoting effect according to the invention is presumably due to the combination of three effects: firstly a cavity network is produced owing to the release of the water-soluble and extremely finely distributed substances, from which the microorganisms can simultaneously attack the surrounding polymer matrix from the outside and, at many points, from the inside. Secondly, the cavity network appears to store moisture very well because of the capillary forces and the hydrophilic properties of the polymers. Thirdly, ammonium and phosphate ions are provided, for example, which promote the microbiological growth and therefore accelerate the biodegradation owing to the growth of microorganisms. This assumption is supported by the literature, according to which not only are phosphate and ammonium ions conducive to the growth of microorganisms, but also sulphate, nitrate, calcium, magnesium, potassium and iron ions (see Ullmann's Biotechnology and Biochemical Engineering, Weinheim 2007, page 29). The particle size of components a) and b), which have to be finely distributed in the biodegradable plastic, namely in the micron range, is also helpful. Thus, the small particle size helps to not substantially impair the strength characteristics of the polymer body. If the products from the biodegradable plastic according to the invention are very thin, such as, for example, fibres and films, a particle diameter of about 2 µm is particularly favourable for optimal quality and processability.

Although it is not necessary for the person skilled in the art to have disclosed to him how he obtains the small particle size of the components a) and b), nevertheless it is pointed out here that the procedure is advantageously as follows: the micronisation of the small water-soluble materials, like the salts mentioned, is carried out in non-aqueous solvents (such as, for example, acetone, ethyl acetate, ether, isopropanol, ethanol, etc.) in a ball mill. In order to avoid re-agglomeration, part of the matrix polymer that is soluble in the solvent is already added during the grinding. The starting suspension for a dry spinning or film casting process can be obtained from this suspension by mixing with additional solvent and polymer material. Thus, for example, for the system cellulose acetate, acetone/sugar, $(NH_4)_2HPO_4$, $K_2SO_4$, the solids were mixed as a 10 to 20% by weight mixture in acetone with 4 to 8% by weight cellulose diacetate, in order to then produce in a separate mixing vessel by adding further acetone and cellulose acetate, a weight ratio of approximately 70:28:1.5 of acetone:cellulose diacetate:micronised solids as the starting suspension for a dry spinning process. The further processing of this suspension in filters and fine spinning nozzles succeeded without any clogging. The threads exhibited only an extremely strength loss. Thus, the samples recorded in Table I were also produced according to this procedure.

If the micronised substances a) and b) are to be introduced into a biodegradable plastic that is processed in the molten state, a wet grinding is firstly carried out, as described above, in a water-free solvent in a ball mill. The polymer fraction is then slightly increased and the suspension dried, for example, on a roller dryer or spray dryer. If the plastic is not soluble in common solvents, such as acetone, ethyl acetate, butyl acetate, etc., the product to be ground may, for example, be ground in acetone and stabilised with 1 to 5% cellulose acetate. The material obtained can then be homogeneously distributed as the master batch together with the polymers in the mixing zone of an extruder. Alternatively, the completely ground suspension can be incorporated in the matrix polymer in a kneading machine, then dried and formed again like normal granulate in melt.

The use of the biodegradable plastic according to the invention is particularly favourable when used in composite materials, for example for degradable flowerpots, which are buried together with the plant. Dried reeds or the like can often be used as the second component in composite materials of this type. Thus, it is advantageous if the degradation speed of the flowerpot walls is increased and the optimal degradation speed in this application is adjusted with the correct dosage of water-soluble material and nutrient supply. At the same time, the plant itself can profit from the nutrient supply and optionally from the plant protecting agent, which is gradually released with the biodegradation of the plastic component.

The invention will be described in more detail below with the aid of an example.

EXAMPLE

This example relates to the production of cellulose acetate fibres, which contain 5% by weight saccharose and 1% by weight sodium ammonium hydrogen phosphate, in order to thereby test the biodegradability.

Suspension of Saccharose:

500 g saccharose were micronised in 2000 g acetone into d90<1.9 μm, a Bachofen Multilab KD 0.31 (ball mill) with zirconium oxide balls with a diameter of 0.8 mm being used. The suspension was stabilised against sedimentation by the addition of 6% by weight cellulose acetate.

Suspension of Sodium Ammonium Hydrogen Phosphate B:

100 g sodium ammonium hydrogen phosphate were micronised in 900 g acetone to the d90 value<1 μm using a ball mill. The suspension was stabilised against sedimentation by the addition of 6% by weight cellulose acetate.

Production of a Spinning Solution:

to produce the spinning solution, a mixing container with a stirrer was used. 1 part by weight of a suspension of saccharose and 0.4 parts by weight of the suspension of the sodium ammonium hydrogen phosphate were added to a solution of 21.93 parts by weight cellulose acetate in 58.81 parts by weight acetone, resulting in a mixture with a total solid content of 26% by weight. The solid content could be sub-divided as follows: 94% by weight cellulose acetate, 5% by weight saccharose and 1% by weight sodium ammonium hydrogen phosphate. The water content of the spinning solution was adjusted to 2 to 5% by weight and stirred for 12 hours.

The spinning solution was filtered (<4 μm), a filter-medium filtration taking place. The residue on the filter was insignificant and only related to the total quantity of additives in the spinning solution.

Using this spinning solution, a dry spinning operation was carried out by means of spinning nozzles with triangularly shaped nozzles in order to supply 210 3 dtex filaments with a trilobal cross section. After the drying, a rectangular textile area of 2 cm×1 cm with a weight per unit area of 0.15 g/cm² was crocheted from these filaments. These test specimens were buried in earth to EN ISO 11721-1. After specific times, samples were removed to check the weight and to determine the acetyl value.

The method described above represents a particularly advantageous procedure. It was modified to the extent that apart from 5% by weight saccharose, 0.1 or 0.5% by weight $Na(NH_4)_2PO_4$ were present in the finally obtained biodegradable plastic, while in a further test, apart from 5% by weight saccharose and 0.1% by weight $Na(NH_4)_2PO_4$, 1% by weight $TiO_2$(VLP7000) was also present. The measuring results are recorded in the following Table I.

TABLE I (Degradation speed of cellulose acetate filter tow in the earth burying test, expressed as a percentage weight loss)

| Material | Mean weight loss (%) (after 4 weeks) | Mean weight loss (%) (after 8 weeks) | Mean weight loss (%) (after 12 weeks) |
|---|---|---|---|
| 5% saccharose; 0.1% $Na(NH_4)_2PO_4$ | 10.64 | 33.39 | 50.63 |
| 5% saccharose; 0.5% $Na(NH_4)_2PO_4$ | 19.49 | 44.37 | 72.9 |
| No additives (comparison) | 4.54 | 16.81 | 25.29 |
| 5% saccharose; 0.1% $Na(NH_4)_2PO_4$; 1% $TiO_2$(VLO7000) | 10.66 | 26.67 | 51.08 |
| Cotton | 68.58 | 90.31 | 87.32 |

Note:
Determination of the degradation speed to EN ISO 11721-1

Mean values of the percentage weight loss after 4 weeks, 8 weeks and 12 weeks are designated in Table I.

The invention claimed is:

1. A biodegradable plastic with an increased biodegradation speed, comprising: a polymer, and
   (a) approximately 0.1 to 40% by weight of finely distributed particles of a biodegradable, water-soluble, organic component with a mean particle size of less than 10 μm and
   (b) finely distributed particles of a water-soluble, inorganic component containing N, P and/or S, promoting the growth of microorganisms and with a mean particle size of less than 10 μm,
   wherein the component (a) is a water-soluble saccharide, a water-soluble organic acid and/or a water-soluble nitrogen compound,
   wherein the water-soluble saccharide is saccharose, glucose, maltose and/or lactose,
   wherein the water-soluble organic acid is oxalic acid, malonic acid, glutaric acid, adipic acid, malic acid, tartaric acid, citric acid, ascorbic acid and/or amino carboxylic acids, and
   wherein the water-soluble organic nitrogen compound is urea, guanidine, hexamethylenetetramine, glycine and/or alanine;
   wherein the polymer is a cellulose ester, polylactide, polycaprolactone and/or polyhydroxybutyric acid.

2. The biodegradable plastic according to claim 1, wherein the component (a) has a mean particle size of less than approximately 5 μm.

3. The biodegradable plastic according to claim 1, wherein the component (a) is contained in the plastic in a quantity of approximately 1 to 20% by weight.

4. The biodegradable plastic according to claim 1, wherein the component (b) has a mean particle size of less than 5 μm.

5. The biodegradable plastic according to claim 1, wherein the component (b) is present in the form of one or more salts containing Na, $NH_4$, K, Mg, Ca and/or Fe.

6. The biodegradable plastic according to claim 5, wherein the one or more salts is present in the form of $Na(NH_4)_2PO_4$, $NaNH_4HPO_4$, $NaH_2PO_4$, $Na_2SO_4$, $(NH_4)_2SO_4$, $NH_4NO_3$, $NaNO_3$, $MgSO_4$, $KH_2PO_4$, $FeSO_4$ and/or $NH_4Cl$, individually or in a mixture.

7. The biodegradable plastic according to claim 1, wherein the component (b) is present in the biodegradable plastic in a quantity of approximately 0.01 to 20% by weight.

8. The biodegradable plastic according to claim 1, wherein said biodegradable plastic is a molded part, a fiber, a film, a deep-drawn film, an injection-molded article, a thick-walled molded part, a granulate, a microbead, a bead, a vessel, or a flower pot.

9. The biodegradable plastic according to claim 8, wherein the molded part contains controlled-release biocides and/or fertilizers.

10. The biodegradable plastic according to claim 1 in the form of threads, obtained by dry spinning of a suspension comprising components (a) and (b), a solvent, and dissolved polymer.

11. The biodegradable plastic according to claim 1 in the form of a filter tow obtained by dry spinning a suspension comprising components (a) and (b), a solvent, and dissolved polymer to threads and subsequently processing the threads to filter tows.

12. A film obtained by processing a solution or melt of a biodegradable plastic according to claim 1 by flat extrusion or by film blowing to form a film.

* * * * *